US00PP08739P

United States Patent [19]

van Andel

[11] Patent Number: Plant 8,739

[45] Date of Patent: May 17, 1994

[54] ALSTROEMERIA NAMED STALOVE

[75] Inventor: Jacob van Andel, Aalsmeer, Netherlands

[73] Assignee: Van Staaveren B.V., Aalsmeer, Netherlands

[21] Appl. No.: 25,587

[22] Filed: Mar. 3, 1993

[51] Int. Cl.[5] ..... A01H 5/00

[52] U.S. Cl. ..... Plt./87.1

[58] Field of Search ..... Plt. 88.1

*Primary Examiner*—James R. Feyrer

*Attorney, Agent, or Firm*—Tilton, Fallon, Lungmus & Chestnut

[57] ABSTRACT

A new and distinctive Alstroemeria cultivar particularly distinguished by its profuse and recurrent production of very large flowers having an lemon yellow coloration for all of its petals with the exception of Chrysanthemum crimson spots on the two inner lateral petals of the six petals arranged in two concentric circles of three petals per flower; these flowers being carried on erect stems branching from a tall main stem forming a strong upright bush.

1 Drawing Sheet

BACKGROUND OF THE NEW PLANT

This Alstroemeria cultivar originated as a seedling hybrid produced in my nursery at Aalsmeer, The Netherlands, by my crossing of two plants selected from a field of various alstroemeria varieties maintained at my nursery for breeding purposes. This particular seedling was selected from those produced by the hybridization because of its ability to produce in winter. This selected seedling was propagated by me at Aalsmeer by dividing root stock with very satisfactory results and thereafter this selected plant was propagated through several successive generations in the same manner which demonstrated conclusively that the novel characteristics of the originally selected seedling would be maintained from generation to generation and its homogeneity would be firmly established.

DESCRIPTION OF THE DRAWING

My new Alstroemeria plant is illustrated by the accompanying photographic drawing which, in full color, shows the form and coloration of the flowers as they appear with relatively close spacing at the upper end portion of the flowering stem of the plant. The colors shown are as nearly true to these herein specified as is reasonably possible to obtain by conventional photographic procedures.

DESCRIPTION OF THE NEW PLANT

The following is a detailed description of my new Alstroemeria plant as observed from plants grown under greenhouse conditions in Aalsmeer, The Netherlands, with the stated flower colors being according to The R.H.S. Colour Chart of The Royal Horticultural Society of London, England.

THE PLANT

Origin: Seedling.

Parentage:

*Seed parent.*—*84* G 447-2 (unpatented). A yellow colored Alstroemeria.

*Pollen parent.*—85 G 325-1 (unpatented). A yellow colored Alstroemeria.

Both of these parent plants are so identified in my business records maintained at the office of my nursery at Aalsmeer, The Netherlands and the production of the aforementioned seedling are also recorded. The parent plants are both hybrids and are proprietary.

Classification:

*Botanic.*—Alstroemeria hybrid.

*Commercial.*—Alstroemeria hybrid.

Form: An upright bush.

Height: About 150–225 cm.

Growth rate: Flowering in about 3–4 months following the first planting.

Main stem length: 180 cm.

Strength: Strong.

Branching character: The main stem has an umbel in which 4–6 branches (peduncles) are grouped. At the end of the peduncle a flower is situated on a pedicel. Above the peduncle additional pedicels may occur. The number of flowers per branch is 2–3.

Growth: Vigorous.

Foliage:

*Quantity.*—Abundant.

*Number of leaves.*—25–30.

*Size and shape of leaf.*—The leaf is elliptical shaped, about 12–17 cm in length and about 2–3.5 cm in width.

*Margin type.*—Entire.

*Texture.*—Glossy.

*Color.*—Upper side RHS-137A. Under side RHS-137C.

Rhizomes: Yes.

*Color.*—RHS 155D.

*Size.*—10–30 cm.

THE BUD

Size:

*Diameter.*—1–2 cm.

*Length.*—2–4 cm.

Shape: Pear shaped.

Rate of opening: Bud to flower in about 3–5 days.

Color of petals:

*When sepals first divided.*—RHS 13A.

*When petals begin to unfurl.*—RHS 13A.

Slitting: No.

THE FLOWER

Blooming habit: Recurrent and profuse — Spring and Fall.

Size of bloom: Very large.

*Diameter.*—7 cm.

*Depth.*—5 cm.

Borne: Singly.

Shape: When bloom first opens and when it matures the blooms are cup shaped.

Petalage:

*Number of petals.*—Six.

*Arrangement.*—Two concentric circles of three petals.

*Texture.*—Finely crinkled.

*Form.*—Minutely crinkled or creped. The three outer petals are lobed at the apex; the inner petals are substantially obovate.

*Margin type.*—Very finely dentate.

*Apex.*—Pointed.

*Appearance.*—Velvety.

*Remain on stem.*—Three weeks.

*Color.*—Outer petals Body: RHS 13A/B Base: RHS 13B. Reverse Side: RHS 13B. Inside petals Body: RHS 14A. Base: RHS 13B. Reverse side RHS 13A. The two inner lateral petals have 20–40 spots, color RHS 185A.

Discoloration after full bloom: Slightly.

Persistence: The petals of matured flowers do not hang on and dry.

Fragrance: None.

Lasting quality:

*On the plant.*—About 3 weeks.

*As a cut flower.*—About 2 weeks.

Flower stem:

*Length.*—About 12–14 cm.

*Character.*—Upright and strong.

*Color.*—RHS 137B/C.

THE REPRODUCTIVE ORGANS

Stamens:

*Number.*—About Six.

*Arrangement.*—Clustered around the style.

*Anthers.*—Size: 8–10 mm. Color: RHS 13A.

*Filaments.*—Length: About 5 cm. Color: RHS 16A.

*Pollen.*—Color: RHS 15A.

Pistils:

*Number.*—One.

*Styles.*—Length about 4–5 cm (RHS 16A)

*Stigmas.*—RHS 16A/B

Fruit:

*Fertile.*—Yes.

*Shape.*—Round.

*Color.*—RHS 163A.

I claim:

1. A new and distinctive Alstroemeria plant, substantially as herein shown and described.

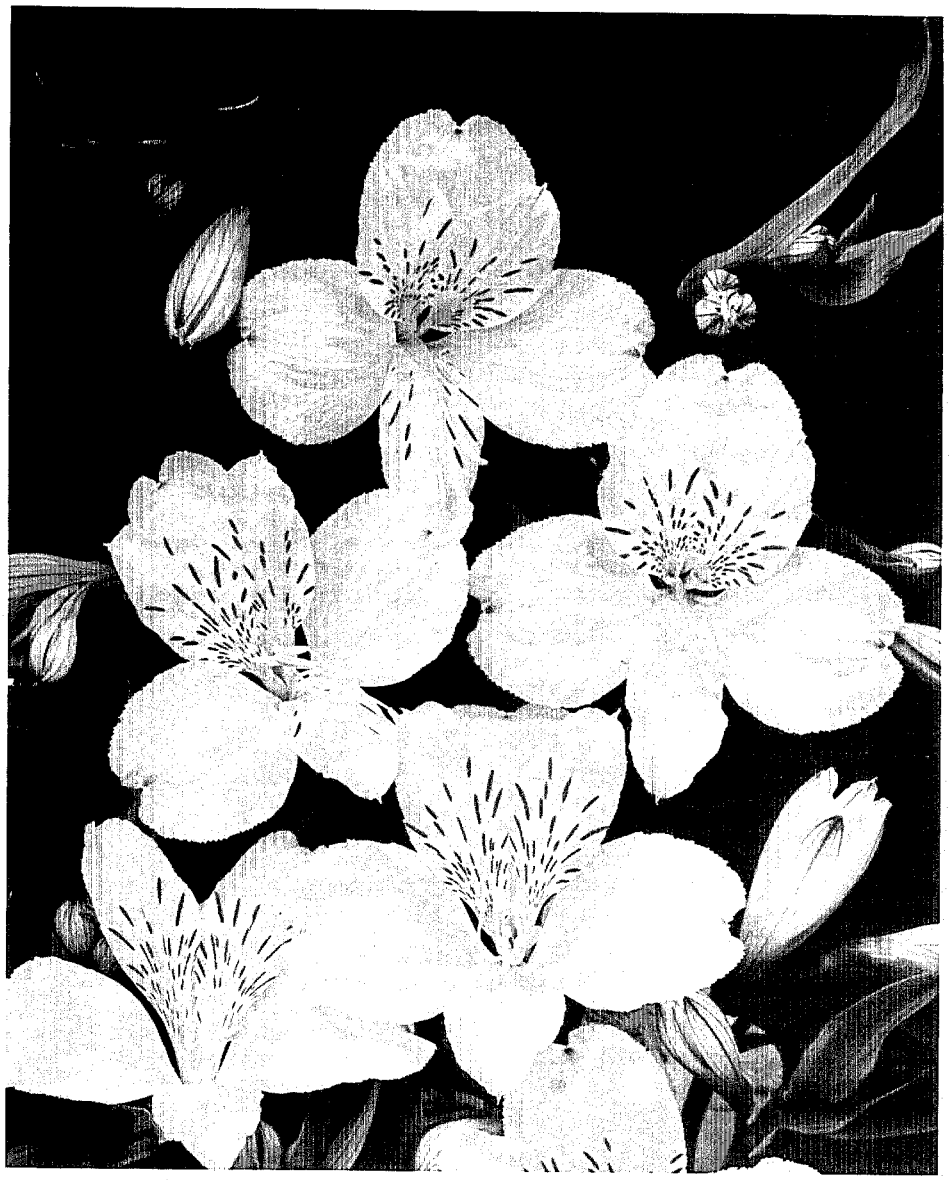

* * * * *